United States Patent [19]

Roper

[11] Patent Number: 4,537,920

[45] Date of Patent: Aug. 27, 1985

[54] 4H-1-BENZOPYRANS AND LUBRICANT COMPOSITIONS CONTAINING SAME

[75] Inventor: Jerry M. Roper, Baton Rouge, La.

[73] Assignee: Ethyl Corporation, Richmond, Va.

[21] Appl. No.: 524,402

[22] Filed: Aug. 18, 1983

[51] Int. Cl.³ ............................................. C10M 1/20
[52] U.S. Cl. ................................ 252/52 R; 549/399; 549/405; 252/407
[58] Field of Search ............. 252/52 R, 407; 549/399, 549/405

[56] References Cited

U.S. PATENT DOCUMENTS 3,796,727  3/1974  Deboer .................................. 549/405
4,210,663  7/1980  Belletire ................................ 549/405

FOREIGN PATENT DOCUMENTS 2055690  5/1971  France .

OTHER PUBLICATIONS

J. Org. Chem., vol. 36, No. 4, "The Preparation and Certain Reactions of 3-Formyl-4H Flavene" by G. A. Reynolds et al., pp. 600–602, 1971.

*Primary Examiner*—Jacqueline V. Howard
*Attorney, Agent, or Firm*—Donald L. Johnson; John F. Sieberth; Patricia J. Hogan

[57] ABSTRACT

4H-1-Benzopyrans are prepared by reacting an aminomethylphenol with an alkali metal hydroxide or an alkaline earth metal hydroxide and a 1,3-diketone. The products are useful as antioxidants.

17 Claims, No Drawings

4H-1-BENZOPYRANS AND LUBRICANT COMPOSITIONS CONTAINING SAME

TECHNICAL FIELD

This invention relates to novel 4H-1-benzopyrans and the preparation and uses thereof as antioxidants for oxidizable organic materials when such materials are exposed to oxidative degradative conditions.

THE INVENTION

The materials of the invention are prepared by reacting an aminomethylphenol with a 1,3-diketone and an alkali metal hydroxide or an alkaline earth metal hydroxide. Thus, in one embodiment of the invention there is provided a novel process for the preparation of compounds having a benzopyranyl moiety which comprises reacting an aminomethylphenol with a 1,3-diketone and an alkali metal hydroxide or an alkaline earth metal hydroxide.

The process can be illustrated schematically by the following equations. Compounds having the general structural formula:

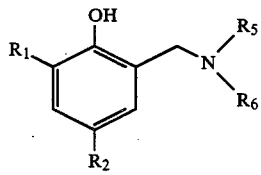

are reacted with compounds of the general formula:

and an alkali metal hydroxide or an alkaline earth metal hydroxide to yield 4H-1-benzopyrans having the general structural formula:

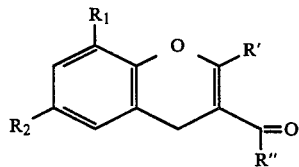

In the structural formulas above $R_1$, $R_2$, $R_3$, $R_4$, $R_5$ and $R_6$ are the same or different and are hydrogen or hydrocarbyl radicals, substituted hydrocarbyl radicals or hydrocarbyloxy radicals. $R'$ may correspond to either $R_3$ or $R_4$ of the 1,3-diketone reactant and $R''$ corresponds to the other of $R_3$ or $R_4$. In practice, where $R_3$ and $R_4$ differ from each other, the 4H-1-benzopyran produced will comprise a mixture of both such species.

Preferably, the hydrocarbyl radicals are those that contain up to about 20 carbon atoms. The more preferred hydrocarbyl radicals are the lower alkyls of up to about 10 carbon atoms. The most preferred hydrocarbyls are methyl and ethyl. For the purposes of this invention a hydrocarbyl radical can be defined as an organic group solely composed of hydrogen and carbon atoms. Some non-limiting representative examples of hydrocarbyl radicals are alkyl, cycloalkyl, alkenyl, aralkyl, alkaryl, and aryl.

Examples of suitable alkyl groups are methyl, ethyl, n-propyl, isopropyl, n-butyl, isobutyl, sec-butyl, tert-butyl, n-amyl, and the various isomers thereof, and likewise the corresponding straight and branched chain isomers of hexyl, heptyl, octyl, nonyl, decyl, undecyl, dodecyl, and the like.

Some examples of cycloalkyl groups are cyclopropyl, cyclobutyl, cyclopentyl, cyclohexyl, cycloheptyl, cyclooctyl, cyclononyl, cyclodecyl, cycloundecyl, cyclododecyl, and the like. They may also be such cycloaliphatic groups as α-cyclopropyl-ethyl, α-cyclobutyl-propyl, β-cyclobutyl-propyl, and similar alkyl derivatives of the higher cycloalkyls.

Some examples of alkenyl groups are ethenyl, 1-propenyl, 2-propenyl, isopropenyl, 1-butenyl, 2-butenyl, 3-butenyl, and the corresponding branched-chain isomers thereof as for example, 1-isobutenyl, 2-isobutenyl, 2-sec-butenyl, including 1-methylene-2-propenyl, and the various isomers of pentenyl, hexenyl, heptenyl, octenyl, nonenyl, decenyl, undecenyl, and dodecenyl, including 3,3-dimethyl-1-butenyl, 2,3-dimethyl-1-butenyl, 2,3-dimethyl-2-butenyl, 2,3-dimethyl-3-butenyl, 1-methyl-1-ethyl-2-propenyl, and the like.

Examples of alkaryl groups are tolyl, 2,3-xylyl, 2,4-xylyl, 2,5-xylyl, 2,6-xylyl, 3,4-xylyl, 3,5-xylyl; o, m, and p-cumenyl, mesityl, o, m, and p-ethylphenyl, 2-methyl-1-naphthyl, 3-methyl-naphthyl, 4-methyl-1-naphthyl, 5-methyl-2-naphthyl, 6-methyl-3-naphthyl, 7-methyl-1-naphthyl, 8-methyl-4-naphthyl, 1-ethyl-2-naphthyl, and its various positional isomers and the like.

Examples of aryl groups which may be present in the above general formula are phenyl, naphthyl, and the like.

Examples of aralkyl groups are benzyl, phenylethyl, 1-phenylpropyl, 2-phenylpropyl, 3-phenylpropyl, 1- and 2-isomers of phenylisopropyl, 1-, 2-, and 3-isomers of phenylbutyl, and the like.

The substituted hydrocarbyl radicals are hydrocarbyl radicals which contain substituents that are innocuous (i.e., inert) to the reaction conditions. That is, suitable substituents are those that will not interfere with the formation of the products produced by the process of the invention or change the identity of the products produced by the process of the invention at the reaction conditions observed for the process. Suitable substituents include halogen, hydroxyl, carboxyl, amino, or amide radicals.

As mentioned above, the hydrocarbyl groups may be halogen substituted. Thus, chlorine, bromine, iodine, and fluorine may be substituted on the alkyl, cycloalkyl, alkenyl, alkaryl, aryl, and aralkyl groups which are present. Non-limiting examples of such substituted groups are chloromethyl, chloroethyl, bromoethyl, 2-fluoro-1,2-dibromoethyl, 1-iodopropyl, 2-fluoropropyl, 1-chlorobutyl, 2-bromobutyl, 2-iodo-2-methylpropyl, 1-chloropentyl, 3-fluoro-2-methylbutyl, 3-iodo-2-methyl-butyl, 1-chloro-2,2-dimethylpropyl, 2-chloroheptyl, 3-fluorononyl, 1-chlorododecyl, and the like. Examples of halogenated cycloalkyl groups are chlorocyclopropyl, chlorocyclohexyl, 1,2-dichlorohexyl, bromocyclobutyl, iodocyclohexyl, and the like.

Examples of halogen-substituted alkenyl groups are bromoethenyl, chloroethenyl, iodoethenyl, 1-bromododecenyl, and the like.

Examples of halogenated alkaryl groups are chloro-o-tolyl, chloro-p-tolyl, chloro-m-tolyl, 2-bromo-3,4-xylyl, 4-bromo-2,3-xylyl, 5-bromo-2,4-xylyl, 2-bromo-4,5-xylyl, 3-bromomesityl, chloro(methyl)-1-naphthyl, iodo(ethyl)-1-naphthyl, all positional isomers of the above, and the like.

Examples of halogen substituted aryl groups are bromophenyl, 2-bromo-1-naphthyl, 3-bromo-1-naphthyl and all positional isomers thereof, 2,4-dibromophenyl, 2,3-dibromophenyl, 2,5-dibromophenyl, 2,3,4,5-tetrabromophenyl, 2,3,5,6-tetrabromophenyl, pentabromophenyl, all isomers of chlorophenyl, and all isomers of multichlorophenyl, 2-chloro-1-naphthyl and the remaining isomers thereof, 2,3-dichloro-1-naphthyl, 2,4-dichloro-1-naphthyl and the remaining positional isomers of dichloronaphthyl, 2,3,4,5-tetrachloro-1-naphthyl.

Amine groups may also be substituted on the hydrocarbyl groups. Some non-limiting illustrative examples of hydrocarbyl groups containing amine substituents are aminomethyl, 2-aminoethyl, 2,2-diaminoethyl, 2-aminoisopropyl, 5-aminopentyl, 1,2-aminododecyl, 1,2-diaminoethyl, 1,5-diaminopentyl, aminocyclobutyl, aminocyclohexyl, 3-amino-1-propen-1-yl, 5-amino-2-penten-1-yl, aminophenyl, (methylamino)phenyl, 2-amino-o-tolyl, 4-amino-m-tolyl, 3-amino-p-tolyl, and other positional isomers, various isomers of diaminophenyl, amino 2,5-xylyl, and various positional isomers thereof, 2-amino-1-naphthyl, 3-amino-1-naphthyl, 2-amino-3-methyl-1-naphthyl, 2,3-diamino-5-ethyl-1-naphthyl, and the like.

The hydrocarbyl groups may contain amide groups which may be illustrated by such non-limiting examples as carbamoylmethyl, 2-carbamoylethyl, 4-carbamoylbutyl, 8-carbamoyl-2-ethyloctyl, 1,4-dicarbamoylbutyl, carbamoylcyclopentyl, carbamoylcyclohexyl, 2-carbamoyl-o-tolyl, 2-carbamoyl-m-tolyl, 3-carbamoyl-p-tolyl, (carbamoylmethyl)phenyl, (2-carbamoylethyl)benzyl, o-, m-, and p-(carbamoylethyl)phenyl, and the like.

Representative examples of some of the 4H-1-benzopyran compounds, functioning as antioxidants, which can be prepared by the process of the present invention include:
  3-acetyl-6,8-di-t-butyl-2-methyl-4H-1-benzopyran,
  3-butyryl-6,8-di-t-butyl-2-methyl-4H-1-benzopyran,
  3-acetyl-6,8-di-t-butyl-2-propyl-4H-1-benzopyran,
  3-caproyl-6,8-di-t-butyl-2-methyl-4H-1-benzopyran,
  3-acetyl-6,8-di-t-butyl-2-pentyl-4H-1-benzopyran,
  3-isobutyryl-6,8-di-t-butyl-2-isopropyl-4H-1-benzopyran,
  3-heptylyl-6,8-di-t-butyl-2-methyl-4H-1-benzopyran,
  3-acetyl-6,8-di-t-butyl-2-hexyl-4H-1-benzopyran,
  3-caprylyl-6,8-di-t-butyl-2-methyl-4H-1-benzopyran,
  3-acetyl-6,8-di-t-butyl-2-heptyl-4H-1-benzopyran,
  3-heptylyl-6,8-di-t-butyl-2-hexyl-4H-1-benzopyran,
  3-acetyl-2,6-dimethyl-8-isopropyl-4H-1-benzopyran,
  3-butyryl-2,6-dimethyl-8-isopropyl-4H-1-benzopyran,
  3-acetyl-6-methyl-8-isopropyl-2-propyl-4H-1-benzopyran,
  3-caproyl-2,6-dimethyl-8-isopropyl-4H-1-benzopyran,
  3-acetyl-6-methyl-8-isopropyl-2-pentyl-4H-1-benzopyran,
  3-isobutyryl-6-methyl-2,8-diisopropyl-4H-1-benzopyran,
  3-heptylyl-2,6-dimethyl-8-isopropyl-4H-1-benzopyran,
  3-acetyl-6-methyl-8-isopropyl-2-hexyl-4H-1-benzopyran,
  3-caprylyl-2,6-dimethyl-8-isopropyl-4H-1-benzopyran,
  3-acetyl-6-methyl-8-isopropyl-2-heptyl-4H-1-benzopyran,
  3-heptylyl-6-methyl-8-isopropyl-2-hexyl-4H-1-benzopyran,
  3-acetyl-2,6-dimethyl-8-t-butyl-4H-1-benzopyran,
  3-butyryl-2,6-dimethyl-8-t-butyl-4H-1-benzopyran,
  3-acetyl-6-methyl-8-t-butyl-2-propyl-4H-1-benzopyran,
  3-caproyl-2,6-dimethyl-8-t-butyl-4H-1-benzopyran,
  3-acetyl-6-methyl-8-t-butyl-2-pentyl-4H-1-benzopyran,
  3-isobutyryl-6-methyl-8-t-butyl-2-isopropyl-4H-1-benzopyran,
  3-heptylyl-2,6-dimethyl-8-t-butyl-4H-1-benzopyran,
  3-acetyl-6-methyl-8-t-butyl-2-hexyl-4H-1-benzopyran,
  3-caprylyl-2,6-dimethyl-8-t-butyl-4H-1-benzopyran,
  3-acetyl-6-methyl-8-t-butyl-2-heptyl-4H-1-benzopyran,
  3-heptylyl-6-methyl-8-t-butyl-2-hexyl-4H-1-benzopyran,
  3-acetyl-6,8-diisopropyl-2-methyl-4H-1-benzopyran,
  3-butyryl-6,8-diisopropyl-2-methyl-4H-1-benzopyran,
  3-acetyl-6,8-diisopropyl-2-propyl-4H-1-benzopyran,
  3-caproyl-6,8-diisopropyl-2-methyl-4H-1-benzopyran,
  3-acetyl-6,8-diisopropyl-2-pentyl-4H-1-benzopyran,
  3-isobutyryl-2,6,8-triisopropyl-4H-1-benzopyran,
  3-heptylyl-6,8-diisopropyl-2-methyl-4H-1-benzopyran,
  3-acetyl-6,8-diisopropyl-2-hexyl-4H-1-benzopyran,
  3-caprylyl-6,8-diisopropyl-2-methyl-4H-1-benzopyran,
  3-acetyl-6,8-diisopropyl-2-heptyl-4H-1-benzopyran,
  3-heptylyl-6,8-diisopropyl-2-hexyl-4H-1-benzopyran,
  3-acetyl-6,8-di-sec-butyl-2-methyl-4H-1-benzopyran,
  3-butyryl-6,8-di-sec-butyl-2-methyl-4H-1-benzopyran,
  3-acetyl-6,8-di-sec-butyl-2-propyl-4H-1-benzopyran,
  3-caproyl-6,8-di-sec-butyl-2-methyl-4H-1-benzopyran,
  3-acetyl-6,8-di-sec-butyl-2-pentyl-4H-1-benzopyran,
  3-isobutyryl-6,8-di-sec-butyl-2-isopropyl-4H-1-benzopyran,
  3-heptylyl-6,8-di-sec-butyl-2-isopropyl-4H-1-benzopyran,
  3-acetyl-6,8-di-sec-butyl-2-hexyl-4H-1-benzopyran,
  3-caprylyl-6,8-di-sec-butyl-2-methyl-4H-1-benzopyran,
  3-acetyl-6,8-di-sec-butyl-2-heptyl-4H-1-benzopyran,
  3-heptylyl-6,8-di-sec-butyl-2-hexyl-4H-1-benzopyran,
  3-acetyl-6-isopropyl-2-methyl-4H-1-benzopyran,
  3-butyryl-6-isopropyl-2-methyl-4H-1-benzopyran,
  3-acetyl-6-isopropyl-2-propyl-4H-1-benzopyran,
  3-caproyl-6-isopropyl-2-methyl-4H-1-benzopyran,
  3-acetyl-6-isopropyl-2-pentyl-4H-1-benzopyran,
  3-isobutyl-2,6-diisopropyl-4H-1-benzopyran,
  3-heptylyl-6-isopropyl-2-methyl-4H-1-benzopyran,
  3-acetyl-6-isopropyl-2-hexyl-4H-1-benzopyran,
  3-caprylyl-6-isopropyl-2-methyl-4H-1-benzopyran,
  3-acetyl-6-isopropyl-2-heptyl-4H-1-benzopyran,
  3-heptylyl-6-isopropyl-2-hexyl-4H-1-benzopyran,
  3-acetyl-6-t-butyl-2-methyl-4H-1-benzopyran,
  3-butyryl-6-t-butyl-2-methyl-4H-1-benzopyran, 3-acetyl-6-t-butyl-2-propyl-4H-1-benzopyran,
3-caproyl-6-t-butyl-2-methyl-4H-1-benzopyran,
3-acetyl-6-t-butyl-2-pentyl-4H-1-benzopyran,
3-isobutyryl-6-t-butyl-2-isopropyl-4H-1-benzopyran,
3-heptylyl-6-t-butyl-2-methyl-4H-1-benzopyran,
3-acetyl-6-t-butyl-2-hexyl-4H-1-benzopyran,
3-caprylyl-6-t-butyl-2-methyl-4H-1-benzopyran,
3-acetyl-6-t-butyl-2-heptyl-4H-1-benzopyran,
3-heptylyl-6-t-butyl-2-hexyl-4H-1-benzopyran,
3-acetyl-6-ethyl-8-t-butyl-2-methyl-4H-1-benzopyran,
3-butyryl-6-ethyl-8-t-butyl-2-methyl-4H-1-benzopyran,
3-acetyl-6-ethyl-8-t-butyl-2-propyl-4H-1-benzopyran,
3-caproyl-6-ethyl-8-t-butyl-2-methyl-4H-1-benzopyran,
3-acetyl-6-ethyl-8-t-butyl-2-pentyl-4H-1-benzopyran,
3-isobutyryl-6-ethyl-8-t-butyl-2-isopropyl-4H-1-benzopyran,
3-heptylyl-6-ethyl-8-t-butyl-2-methyl-4H-1-benzopyran,
3-acetyl-6-ethyl-8-t-butyl-2-hexyl-4H-1-benzopyran,
3-caprylyl-6-ethyl-8-t-butyl-2-methyl-4H-1-benzopyran,
3-acetyl-6-ethyl-8-t-butyl-2-heptyl-4H-1-benzopyran,
3-heptylyl-6-ethyl-8-t-butyl-2-hexyl-4H-1-benzopyran,
3-acetyl-6,8-diheptyl-2-methyl-4H-1-benzopyran,
3-butyryl-6,8-diheptyl-2-methyl-4H-1-benzopyran,
3-acetyl-6,8-diheptyl-2-propyl-4H-1-benzopyran,
3-isobutyryl-6,8-diheptyl-2-isopropyl-4H-1-benzopyran,
3-heptyl-6,8-diheptyl-2-methyl-4H-1-benzopyran,
3-acetyl-6,8-diheptyl-2-hexyl-4H-1-benzopyran,
3-caprylyl-6,8-diheptyl-2-methyl-4H-1-benzopyran,
3-acetyl-2,6,8-triheptyl-2-methyl-4H-1-benzopyran,
3-heptylyl-6,8-diheptyl-2-hexyl-4H-1-benzopyran,
3-acetyl-6-ethyl-2,8-dimethyl-4H-1-benzopyran,
3-butyryl-6-ethyl-2,8-dimethyl-4H-1-benzopyran,
3-acetyl-6-ethyl-8-methyl-2-propyl-4H-1-benzopyran,
3-caproyl-6-ethyl-2,8-dimethyl-4H-1-benzopyran,
3-acetyl-6-ethyl-8-methyl-2-pentyl-4H-1-benzopyran,
3-isobutyryl-6-ethyl-8-methyl-2-isopropyl-4H-1-benzopyran,
3-heptylyl-6-ethyl-2,8-dimethyl-4H-1-benzopyran,
3-acetyl-6-ethyl-8-methyl-2-hexyl-4H-1-benzopyran,
3-caprylyl-6-ethyl-2,8-dimethyl-4H-1-benzopyran,
3-acetyl-6-ethyl-8-methyl-2-heptyl-4H-1-benzopyran,
3-heptylyl-6-ethyl-8-methyl-2-hexyl-4H-1-benzopyran,
3-acetyl-6-t-butyl-8-heptyl-2-methyl-4H-1-benzopyran,
3-butyryl-6-t-butyl-8-heptyl-2-methyl-4H-1-benzopyran,
3-acetyl-6-t-butyl-8-heptyl-2-propyl-4H-1-benzopyran,
3-caproyl-6-t-butyl-8-heptyl-2-methyl-4H-1-benzopyran,
3-acetyl-6-t-butyl-8-heptyl-2-pentyl-4H-1-benzopyran,
3-isobutyryl-6-t-butyl-8-heptyl-2-isopropyl-4H-1-benzopyran,
3-heptylyl-6-t-butyl-8-heptyl-2-methyl-4H-1-benzopyran,
3-acetyl-6-t-butyl-8-heptyl-2-hexyl-4H-1-benzopyran,
3-caprylyl-6-t-butyl-8-heptyl-2-methyl-4H-1-benzopyran,
3-acetyl-2,6,8-triheptyl-2-methyl-4H-1-benzopyran,
3-heptylyl-6-t-butyl-8-heptyl-2-hexyl-4H-1-benzopyran,
3-acetyl-2,6-dimethyl-8-ethyl-4H-1-benzopyran,
3-butyryl-2,6-dimethyl-8-ethyl-4H-1-benzopyran,
3-acetyl-6-methyl-8-ethyl-2-propyl-4H-1-benzopyran,
3-caproyl-2,6-dimethyl-8-ethyl-4H-1-benzopyran,
3-acetyl-6-methyl-8-ethyl-2-pentyl-4H-1-benzopyran,
3-isobutyryl-6-methyl-8-ethyl-2-isopropyl-4H-1-benzopyran,
3-heptylyl-2,6-dimethyl-8-ethyl-4H-1-benzopyran,
3-acetyl-6-methyl-8-ethyl-2-hexyl-4H-1-benzopyran,
3-caprylyl-2,6-dimethyl-8-ethyl-4H-1-benzopyran,
3-acetyl-6-methyl-8-ethyl-2-heptyl-4H-1-benzopyran,
3-heptylyl-6-methyl-8-ethyl-2-hexyl-4H-1-benzopyran Representative examples of aminomethylphenol reactants which may be employed in the practice of the present process include:

N,N-dimethyl,2-aminomethylphenol,
N,N-dimethyl,4,6-di-t-butyl-2-aminomethylphenol,
N,N-dimethyl,4-methyl-6-isopropyl-2-aminomethylphenol,
N,N-dimethyl,4-methyl-6-t-butyl-2-aminomethylphenol,
N,N-dimethyl,4,6-diisopropyl-2-aminomethylphenol,
N,N-dimethyl,4-sec-butyl-2-aminomethylphenol,
N,N-dimethyl4-isopropyl-2-aminomethylphenol,
N,N-dimethyl,4-t-butyl-2-aminomethylphenol,
N,N-diethyl,4,6-di-t-butyl-2-aminomethylphenol,
N,N-dioctyl,4,6-di-t-butyl-2-aminomethylphenol,
N,N-dioctyl,4-ethyl-6-t-butyl-2-aminomethylphenol,
N,N-dioctyl,4,6-diheptyl-2-aminomethylphenol,
N,N-dioctyl,4-ethyl-6-methyl-2-aminomethylphenol,
N,N-dioctyl,4-t-butyl-6-heptyl-2-aminomethylphenol,
N-ethyl,N-methyl,4,6-di-t-butyl-2-aminomethylphenol,
N-octyl,N-methyl,4-methyl-6-ethyl-2-aminomethylphenol,
3,5-di-t-butyl-2-hydroxybenzylpiperidine,
3,5-di-t-butyl-2-hydroxybenzylmorpholine, and
3,5-di-t-butyl-2-hydroxybenzylpyrrolidine.

Representative examples of 1,3-diketone reactants which can be used in the practice of the present process include:

2,4-pentanedione,
2,4-heptanedione,
4,6-nonanedione,
2,6-dimethyl-3,5-heptanedione,
1-hexyl-1,3-butanedione,
1-hexyl-2,4-pentanedione, and
1,3-dihexyl-1,3-propanedione.

Alkali metal hydroxide and alkaline earth metal hydroxide agents which can be used as basic agents in the instant process include: LiOH, NaOH, KOH, RbOH, Ca(OH)$_2$, Ba(OH)$_2$ and Mg(OH)$_2$.

The process of the invention is carried out by reacting the aminomethylphenol starting material with at least 1 molar equivalent of diketone reactant and 1 molar equivalent of alkali metal hydroxide or alkaline earth metal hydroxide. However, an excess of either or both diketone or hydroxide reactant can be used in the process, if desired. A preferred range of diketone reactant to aminomethylphenol reactant is from about 1 to 10 moles of diketone per mole of aminomethylphenol. A preferred range of alkali metal hydroxide or alkaline earth metal hydroxide reactant to aminomethylphenol reactant ranges from about 1 to 10 moles of hydroxide per mole of aminomethylphenol.

The use of a solvent for the reaction mixture is not generally required, since an excess of 1,3-diketone reactant can be conveniently used to serve both as a reactant and solvent in the instant process. However, if desired, a solvent which is inert under the reaction condition, i.e., those solvents which do not enter into the reaction, may be added to the reaction vessel. Useful solvents comprise aprotic solvents which include ethers such as diethyl ether, dibutyl ether, 1-ethoxyhexane, tetrahydrofuran, 1,4-dioxane, 1,3-dioxolane, diglyme, 1,2-diethyoxyethane, etc. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc. Additionally, lower alkanols having up to about 8 carbon atoms also may be used. These include methanol, ethanol, n-propanol, isopropyl alcohol, n-butanol, sec-butyl alcohol, t-butyl alcohol, n-pentanol, isopentyl alcohol, n-hexanol, isohexyl alcohol and n-octanol.

The amount of solvent which may be used can be expressed as a volume ratio of solvent to aminomethylphenol reactant. Suitable volume ratios of solvent to aminomethylphenol reactant can range from about 0/1 to about 500/1 and preferably from about 1/1 to about 300/1.

The mode of addition in the process is not particularly critical. Accordingly, it is convenient to add the aminomethylphenol reactant to a mixture of the other materials, add the 1,3-diketone component to a mixture of the other materials, add the alkali metal hydroxide or alkaline earth metal hydroxide reactant to a mixture of the other materials, add the reactants to a mixture of the aminomethylphenol and solvent, introduce all ingredients simultaneously into the reaction zone or the like.

The process should be carried out for a time sufficient to convert as much of the aminomethylphenol reactant to the corresponding 4H-1-benzopyran as possible. It is believed that the length of time for optimum yield will depend primarily upon the reaction temperature and the particular solvent, if any, used in the reaction. In general, yields of 4H-1-benzopyran are obtained in from about two to about twenty-four hours.

Although the reaction will proceed at a very slow rate at ambient temperatures, it is convenient to conduct the reaction at an elevated temperature of at least about 50° C. up to just short of the decomposition temperature of any of the reactants or the products. Ambient atmospheric pressure can be used or pressures lower or higher than ambient pressures can be used. However, there is no advantage to using less than ambient pressure. Higher than ambient pressure conditions are usually used if temperatures higher than the boiling point at atmospheric conditions of the reaction mixture are being used. However, by proper choice of a solvent to form the liquid phase desired, temperatures can be reached within the range of about 50° C. up to the reflux temperature of the reaction mixture at ambient atmospheric conditions which give a suitable reaction rate.

Although not required, the process can be conducted in a substantially anhydrous reaction system, and accordingly, the components of the reaction system are brought together and maintained under a substantially dry, inert atmosphere. By "substantially anhydrous" is meant a reaction system wherein the total amount of water present is no more than about 5 percent by weight, based on the reaction mixture.

The process may readily be conducted in a batchwise, semi-batch or continuous manner and in conventional equipment.

The 4H-1-benzopyran product is easily separated from the reaction mixture by such means as distillation, extraction, crystallization and other methods known to those skilled in the chemical processing art.

The 4H-1-benzopyran compounds prepared by the process of this invention are believed to be novel compounds. Thus, another embodiment of the present invention is directed to novel 4H-1-benzopyran compounds having the general structural formula:

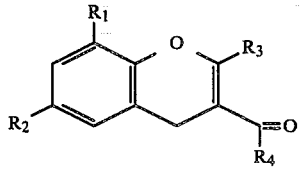

wherein $R_1$, $R_2$, $R_3$, and $R_4$ are the same or different and are hydrogen, hydrocarbyl radicals, substituted hydrocarbyl radicals or hydrocarbyloxy radicals.

The 4H-1-benzopyran proudcts prepared by the process of this invention also are believed to have antioxidant properties and are capable of stabilizing polymers normally subject to oxidative degradation when incorporated into the polymers using conventional techniques such as by addition to polymer lattices; or by addition to solid polymers on a mill or in a Banbury. Further, the compounds of this invention are effective antioxidants in both unleaded and leaded gasolines made from a wide variety of base stocks and for engine and industrial oils which are derived from crude petroleum or produced synthetically.

Thus, in another embodiment of the present invention there is provided a liquid hydrocarbon fuel of the gasoline boiling range for use in spark ignited internal combustion engines normally susceptible to deterioration in the presence of oxygen containing, in an amount sufficient to inhibit such deterioration, compounds of the general formula:

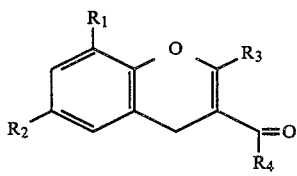

wherein $R_1$, $R_2$, $R_3$, and $R_4$ are the same or different and are hydrogen, hydrocarbyl radicals, substituted hydrocarbyl radicals or hydrocaryloxy radicals.

In a still further embodiment of the present invention there is provided a lubricating oil normally susceptible to oxidative deterioration containing a small antioxidant quantity of a compound of the general formula:

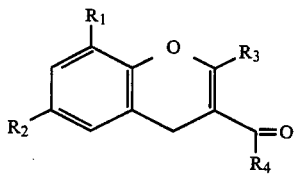

wherein $R_1$, $R_2$, $R_3$, and $R_4$ are the same or different and are hydrogen, hydrocarbyl radicals, substituted hydrocarbyl radicals or hydrocarbyloxy radicals.

The practice of this invention will be still further apparent by the following illustrative examples.

EXAMPLE I

Preparation of 3-Acetyl-6,8-Di-t-Butyl-2-Methyl-4H-1-Benzopyran

N,N-Dimethyl-2-aminomethyl-4,6-di-t-butylphenol (1.32 g; 5 mmols), sodium hydroxide (0.3 g; 7.5 mmols) and acetylacetone (15 mLs) were charged to a 100 mL round bottom flask and heated to a gentle reflux under a nitrogen atmosphere overnight. The majority of acetylacetone was removed by vacuum distillation. The resultant reaction mixture was cooled to ambient temperature to give a yellow distillation residue which was slurried in 2 N sulfuric acid (30 mLs) and then extracted with diethyl ether (3×30 mLs). The combined ether extract was washed with water (30 mLs), dried (MgSO$_4$) and concentrated to afford 3.0 g of a yellow oil which contained by VPC analysis 19% 3-Acetyl-6,8-di-t-butyl-2-methyl-4H-1-benzopyran, 14% N,N-dimethyl-2-aminomethyl-4,6-di-t-butylphenol and 77% 3,5-di-t-butyl-2-hydroxybenzylacetylacetone as identified by gas chromatography-mass spectroscopy.

EXAMPLE II

Preparation of 3-Acetyl-6,8-Di-t-Butyl-2-Methyl-4H-1-Benzopyran

N,N-Dimethyl-2-aminomethyl-4,6-di-t-butylphenol (0.57 g; 2.2 mmols), sodium hydroxide (0.16 g; 3.3 mmols), acetylacetone (7 mLs) in toluene (20 mLs) were charged to a 100 mL round bottom flask which was equipped with a Dean-Stark trap and heated to a gentle reflux under a nitrogen atmosphere for 7 hours. After cooling to room temperature, the reaction mixture was treated with 2N sulfuric acid (40 mLs), extracted with diethyl ether (30 mLs) and the aqueous and organic layers were separated. The aqueous phase was extracted with diethyl ether (20 mLs) and the combined organic portion was dried (MgSO$_4$) and concentrated in vacuo to afford a brown semi-solid product which contained by VPC analysis 9% 3-acetyl-6,8-di-t-butyl-2-methyl-4H-1-benzopyran, 4% N,N-dimethyl-2-aminomethyl-4,6-di-t-butylphenol and 88% 3,5-di-t-butyl-2-hydroxybenzylacetylacetone as identified by gas chromatography-mass spectroscopy.

Having disclosed the process of the present invention, one skilled in the art can readily envision various modifications and changes which are nevertheless within the scope of the invention. Therefore, it is desired that the process of this invention be limited only by the lawful scope of the appended claims.

I claim:

1. A process which comprises reacting one molar proportion of an aminomethylphenol with about 1–10 molar proportions of a 1,3-diketone and about 1–10 molar proportions of an alkali or alkaline earth metal hydroxide at a temperature of at least about 50° C. and a pressure in the range of from atmospheric up to about 1000 psig so as to form a 4H-1-benzopyran.

2. A process which comprises reacting one molar proportion of an aminomethylphenol corresponding to the formula:

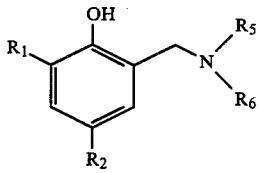

with about 1–10 molar proportions of a 1,3-diketone corresponding to the formula R$_3$COCH$_2$COR$_4$ and about 1–10 molar proportions of an alkali or alkaline earth metal hydroxide at a temperature of at least about 50° C. and a pressure in the range of from atmospheric up to about 1000 psig so as to form a 4H-1-benzopyran corresponding to the formula:

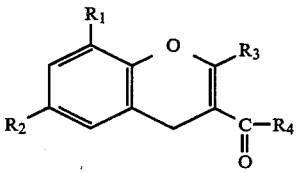

in which formulas $R_1$ and $R_2$ are independently selected from the group consisting of hydrogen and alkyl radicals containing about 1–10 carbons, and $R_3$, $R_4$, $R_5$, and $R_6$ are alkyl radicals containing about 1–10 carbons.

3. The process of claim 2 wherein the alkyl radicals are selected from the group consisting of methyl, ethyl, n-propyl, isopropyl, and butyl.

4. The process of claim 2 wherein the aminomethylphenol is selected from the group consisting of N,N-dimethyl-2-aminomethylphenol, N,N-dimethyl-4,6-di-t-butyl-2-aminomethylphenol, N,N-dimethyl-4-methyl-6-isopropyl-2-aminomethylphenol, N,N-dimethyl-4-methyl-6-t-butyl-2-aminomethylphenol, N,N-dimethyl-4,6-diisopropyl-2-aminomethylphenol, and N,N-dimethyl-4-sec-butyl-2-aminomethylphenol.

5. The process of claim 2 wherein the 1,3-diketone is selected from the group consisting of 2,4-pentanedione, 2,4-heptanedione, 4,6-nonanedione, 2,6-dimethyl-3,5-heptanedione, 1-hexyl-1,3-butanedione, 1-hexyl-2,4-pentanedione, and 1,3-dihexyl-1,3-propanedione.

6. The process of claim 2 wherein the hydroxide is selected from the group consisting of sodium hydroxide, potassium hydroxide, lithium hydroxide, barium hydroxide, magnesium hydroxide, and calcium hydroxide.

7. A lubricating oil composition normally susceptible to oxidative deterioration containing an antioxidant amount of a compound corresponding to the formula:

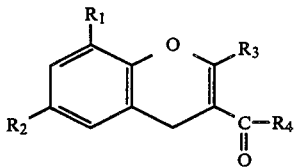

wherein $R_1$ and $R_2$ are independently selected from the group consisting of hydrogen and alkyl radicals containing about 1–10 carbons, and $R_3$ and $R_4$ are independently selected from alkyl radicals containing about 1–10 carbons.

8. A compound corresponding to the formula:

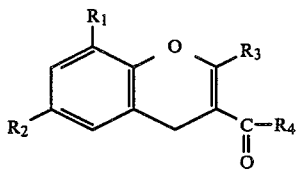

wherein $R_1$ and $R_2$ are independently selected from the group consisting of hydrogen and alkyl radicals containing about 1–10 carbons, and $R_3$ and $R_4$ are independently selected from alkyl radicals containing about 1–10 carbons.

9. The compound of claim 8 wherein the alkyl radicals are selected from the group consisting of methyl, ethyl, n-propyl, isopropyl, and butyl.

10. The process of claim 2 wherein the compound produced is 3-acetyl-6,8-di-t-butyl-2-methyl-4H-1-benzopyran.

11. The process of claim 2 wherein the compound produced is 3-butyryl-6,8-di-t-butyl-2-methyl-4H-1-benzopyran.

12. The process of claim 2 wherein said reaction is carried out in the presence of a solvent which is inert under the reaction conditions.

13. The process of claim 12 wherein the solvent is toluene.

14. The process of claim 2 wherein the reaction is carried out under a substantially dry inert atmosphere.

15. The composition of claim 7 wherein said lubricating oil is a petroleum hydrocarbon oil.

16. The composition of claim 7 wherein said lubricating oil is a synthetic lubricating oil.

17. A compound of claim 9 comprising 3-acetyl-6,8-di-t-butyl-2-methyl-4H-1-benzopyran.

* * * * *